(12) United States Patent
Nesterenko et al.

(10) Patent No.: US 10,464,053 B2
(45) Date of Patent: *Nov. 5, 2019

(54) METHOD FOR MAKING A CATALYST COMPRISING A PHOSPHOROUS MODIFIED ZEOLITE AND USE OF SAID ZEOLITE

(75) Inventors: Nikolai Nesterenko, Nivelles (BE); Delphine Minoux, Nivelles (BE); Cindy Adam, Wierde (BE); Jean-Pierre Dath, Beloeil (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 915 days.

This patent is subject to a terminal disclaimer.

(21) Appl. No.: 14/236,750

(22) PCT Filed: Jul. 25, 2012

(86) PCT No.: PCT/EP2012/064582
§ 371 (c)(1),
(2), (4) Date: Mar. 20, 2014

(87) PCT Pub. No.: WO2013/017499
PCT Pub. Date: Feb. 7, 2013

(65) Prior Publication Data
US 2014/0194662 A1    Jul. 10, 2014

(30) Foreign Application Priority Data

Aug. 3, 2011    (EP) .................................... 11176391

(51) Int. Cl.
| | |
|---|---|
| *B01J 29/06* | (2006.01) |
| *B01J 29/85* | (2006.01) |
| *B01J 29/40* | (2006.01) |
| *B01J 37/02* | (2006.01) |
| *B01J 29/70* | (2006.01) |
| *B01J 29/65* | (2006.01) |
| *B01J 37/10* | (2006.01) |

(Continued)

(52) U.S. Cl.
CPC ............... *B01J 29/85* (2013.01); *B01J 29/40* (2013.01); *B01J 29/405* (2013.01); *B01J 29/655* (2013.01); *B01J 29/70* (2013.01); *B01J 29/7049* (2013.01); *B01J 29/7088* (2013.01); *B01J 29/7096* (2013.01); *B01J 37/0009* (2013.01); *B01J 37/0201* (2013.01); *B01J 37/0209* (2013.01); *B01J 37/10* (2013.01); *B01J 37/28* (2013.01); *C07C 1/20* (2013.01); *C07C 1/22* (2013.01); *C07C 1/24* (2013.01); *C07C 2/08* (2013.01); *C07C 2/66* (2013.01); *C07C 2/864* (2013.01); *C07C 4/06* (2013.01); *C10G 3/49* (2013.01); *C10G 29/205* (2013.01); *C10G 29/22* (2013.01); *B01J 29/65* (2013.01); *B01J 29/7023* (2013.01); *B01J 29/7026* (2013.01); *B01J 29/7038* (2013.01); *B01J 29/7042* (2013.01); *B01J 29/7046* (2013.01); *B01J 2229/186* (2013.01); *B01J 2229/36* (2013.01); *B01J 2229/37* (2013.01); *B01J 2229/42* (2013.01); *C07C 2521/08* (2013.01); *C07C 2527/14* (2013.01); *C07C 2529/40* (2013.01); *C07C 2529/65* (2013.01); *Y02P 20/52* (2015.11); *Y02P 30/42* (2015.11)

(58) Field of Classification Search
CPC ........ B01J 37/10; B01J 37/0009; B01J 37/28; B01J 37/0201; B01J 37/0209; B01J 29/40; B01J 29/65; B01J 29/7023; B01J 29/7026; B01J 29/7038; B01J 29/7042; B01J 29/7046; B01J 29/405; B01J 29/7049; B01J 29/655; B01J 29/7088; B01J 29/7096; B01J 29/70; B01J 2229/36; B01J 2229/37; B01J 2229/42; B01J 2229/186; C07C 2529/40; C07C 2529/65
USPC .................................. 502/65, 71, 75, 77, 85
See application file for complete search history.

(56) References Cited

U.S. PATENT DOCUMENTS

| | | |
|---|---|---|
| 3,274,124 A | 9/1966 | O'Hara |
| 3,909,450 A | 9/1975 | O'Hara |

(Continued)

FOREIGN PATENT DOCUMENTS

| | | |
|---|---|---|
| EP | 0511013 A2 | 10/1992 |
| EP | 0568913 A2 | 11/1993 |

(Continued)

OTHER PUBLICATIONS

Sietsma et al., "Application of ordered mesoporous materials as model supports to study catalyst preparation by impregnation and drying", Scientific Bases for the Preparation of Heterogeneous Catalysts, 2006, pp. 95-102.*

(Continued)

*Primary Examiner* — Elizabeth D Wood
(74) *Attorney, Agent, or Firm* — Albert Shung

(57) ABSTRACT

A method to make a phosphorus modified zeolite can include providing a zeolite having at least one ten member ring, making an ion-exchange, steaming the zeolite, and introducing phosphorus on the zeolite. The zeolite can be mixed with one or more binders and shaping additives, and then shaped. A metal can be introduced, and the catalyst can be washed, calcined, and steamed in an equilibration step. The steaming can be at performed at a steam severity (X) of at least about 2. The steaming can be performed at a temperature above 625° C. The catalyst can be used in alcohol dehydration, olefin cracking, MTO processes, and alkylation of aromatics by alcohols with olefins and/or alcohols.

24 Claims, No Drawings

(51) Int. Cl.

| | | |
|---|---|---|
| *B01J 37/28* | (2006.01) | |
| *C07C 1/20* | (2006.01) | |
| *C07C 1/24* | (2006.01) | |
| *C07C 2/66* | (2006.01) | |
| *C07C 2/86* | (2006.01) | |
| *C07C 4/06* | (2006.01) | |
| *C10G 29/20* | (2006.01) | |
| *C10G 29/22* | (2006.01) | |
| *C10G 3/00* | (2006.01) | |
| *B01J 37/00* | (2006.01) | |
| *C07C 1/22* | (2006.01) | |
| *C07C 2/08* | (2006.01) | |

(56) References Cited

U.S. PATENT DOCUMENTS

| | | | |
|---|---|---|---|
| 3,972,832 A | 8/1976 | Butter et al. | |
| 4,318,801 A * | 3/1982 | Lese | C10G 45/08 208/216 R |
| 4,356,338 A | 10/1982 | Young | |
| 4,988,659 A | 1/1991 | Pecoraro | |
| 5,231,064 A | 7/1993 | Absil et al. | |
| 5,367,100 A * | 11/1994 | Gongwei | B01J 29/40 502/65 |
| 6,797,851 B2 * | 9/2004 | Martens | C07C 1/20 585/639 |
| 8,981,173 B2 * | 3/2015 | Nesterenko | B01J 29/40 585/638 |
| 2006/0106270 A1 | 5/2006 | Glover et al. | |
| 2011/0178259 A1 * | 7/2011 | Nesterenko | B01J 21/08 526/194 |
| 2011/0190563 A1 * | 8/2011 | Grasso | C07C 1/20 585/638 |

FOREIGN PATENT DOCUMENTS

| | | |
|---|---|---|
| EP | 2082802 A1 | 7/2009 |
| EP | 2348004 A1 | 7/2011 |
| WO | 99/29421 A1 | 6/1999 |
| WO | 99/29802 A1 | 6/1999 |
| WO | 99/29803 A1 | 6/1999 |
| WO | 99/29804 A1 | 6/1999 |
| WO | 99/29805 A1 | 6/1999 |
| WO | 99/29806 A1 | 6/1999 |
| WO | 99/29807 A1 | 6/1999 |
| WO | 99/29808 A1 | 6/1999 |
| WO | 00/77122 A1 | 12/2000 |
| WO | 00/77123 A1 | 12/2000 |
| WO | 01/00749 A1 | 1/2001 |
| WO | 02/028987 A1 | 4/2002 |
| WO | 03020667 A1 | 3/2003 |
| WO | 2009022990 A1 | 2/2009 |
| WO | 2009098262 A1 | 8/2009 |
| WO | 2009098267 A1 | 8/2009 |
| WO | 2009098268 A1 | 8/2009 |
| WO | 2009098269 A1 | 8/2009 |
| WO | 2009/156436 * | 12/2009 |

OTHER PUBLICATIONS

Jiang et al., "Highly effective P-modified HZSM-5 catalyst for the cracking of C4 alkanes to produce light olefins", Applied Catalysis A: General, 2008, pp. 176-182.*

W. M. Meier et al., "Atlas of Zeolite Structure Types", Second Revised Edition 1987, Published on behalf of the Structure Commission of the International Zeolite Association by Butterworths (156 pages).

International Search Report issued in PCT/EP2012/064582 dated Dec. 4, 2012 (3 pages).

* cited by examiner

METHOD FOR MAKING A CATALYST COMPRISING A PHOSPHOROUS MODIFIED ZEOLITE AND USE OF SAID ZEOLITE

CROSS-REFERENCE TO RELATED APPLICATIONS

This application claims the benefit of PCT/EP2012/064582, filed on Jul. 25, 2012, which claims priority from EP 11176391.8, filed on Aug. 3, 2011.

FIELD OF THE INVENTION

The present invention relates to a method for making a catalyst comprising a phosphorus modified zeolite and the use of said zeolite. This modified zeolite is of interest in processes wherein said zeolite is operated in presence of steam at high temperature. By way of example one can cite,
the alcohol dehydration to convert at least an alcohol into the corresponding olefin,
the cracking of C4+ olefins (also known as OCP, olefins conversion process) to make a mixture of ethylene and propylene,
the cracking of methanol or dimethylether (also known as MTO) to produce light olefins such as ethylene and propylene as well as heavy hydrocarbons such as butenes,
the alkylation of aromatics by alcohols, by way of example alkylation of benzene or toluene with methanol, ethanol or propanol.

BACKGROUND OF THE INVENTION

An efficient catalyst is a key in industrialization of dehydration of alcohols as well as in the other above processes. One of the early catalysts employed for the dehydration of ethanol was alumina. This catalyst is relatively cheap but needs low space velocity, high reaction temperature and makes a lot of ethane, which needs to be separated. Zeolites, particularly phosphated zeolites, solve a problem with catalyst activity and provide with ethylene fraction, which is closed to polymer grade. Zeolites, particularly phosphated zeolites, solves a problem with catalyst activity. Catalysts comprising a phosphorus modified zeolite (the phosphorus modified zeolite is also referred as P-zeolite) are known. The following prior arts have described various methods to make said catalysts.

US 2006 106270 relates to the use of a dual-function catalyst system in the hydrocarbon synthesis reaction zone of an oxygenate to propylene (OTP) process that operates at relatively high temperatures preferably with a steam diluent and uses moving bed reactor technology. The dual-functional catalyst system comprises a molecular sieve having dual-function capability dispersed in a phosphorus-modified alumina matrix containing labile phosphorus and/or aluminum anions. It is explained that the hydrothermal stabilization effect that is observed when this phosphorus-modified alumima matrix is utilized is caused by migration or dispersion of phosphorus and/or aluminum anions from this matrix into the bound molecular sieve. These anions are then available to repair, anneal and/or stabilize the framework of the molecular sieve against the well-known dealumination mechanism of molecular sieve framework destruction or modification that is induced by exposure to steam at temperatures corresponding to those used in the OTP reaction zone and in the regeneration zone.

U.S. Pat. No. 5,231,064 is directed to a fluid catalyst comprising clay and a zeolite, at least one of which has been treated with a phosphorus containing compound, for example ammonium dihydrogen phosphate or phosphoric acid, and which is spray dried at a low pH, preferably lower than about 3. Said catalysts are deemed to advantageously exhibit reduced attrition.

EP 511013 A2 provides an improved process for the production of C2-C5 olefins from higher olefinic or paraffinic or mixed olefin and paraffin feedstocks. In accordance with this prior art, the hydrocarbon feed materials are contacted with a particular ZSM-5 catalyst at elevated temperatures, high space velocity and low hydrocarbon partial pressure to produce lower olefins. The catalysts is treated with steam prior to use in the hydrocarbon conversion. The preferred method is to heat the catalyst at 500 to 700° C., preferably 550 to 600° C., under 1 to 5 atmospheres, preferably 1.5 to 3 atmospheres steam for 1 to 48 hours, preferably 15 to 30 hours. The active catalyst component is phosphorus-containing ZSM-5 having a surface Si/Al ratio in the range 20-60. Preferably, the phosphorus is added to the formed ZSM-5 as by impregnating the ZSM-5 with a phosphorus compound in accordance with the procedures described, for example, in U.S. Pat. No. 3,972,832. Less preferably, the phosphorus compound can be added to the multicomponent mixture from which the catalyst is formed. The phosphorus compound is added in amount sufficient to provide a final ZSM-5 composition having 0.1-10 wt. % phosphorus, preferably 1-3 wt. %.

The phosphorus-containing ZSM-5 is preferably combined with known binders or matrices such as silica, kaolin, calcium bentonite, alumina, silica aluminate and the like. The ZSM-5 generally comprises 1-50 wt. % of the catalyst composition, preferably 5-30 wt. % and most preferably 10-25 wt. %. There is no introduction of metals such as Ca in the catalyst. ZSM-5 content is below 50%, there is no presteaming step.

EP 568913 A2 describes a method for preparing a ZSM-5 based catalyst adapted to be used in the catalytic conversion of methanol or dimethyl ether to light olefins, wherein it comprises the following consecutive steps:
mixing a zeolite ZSM-5 based catalyst with silica sol and ammonium nitrate solution,
kneading, moulding, drying and calcining the mixture,
exchanging the modified zeolite with a solution of HCl at 70-90° C.,
drying and calcining the H-modified zeolite,
impregnating the H-modified zeolite with phosphoric acid under reduced pressure,
drying and calcining the P-modified zeolite,
impregnating the P-modified zeolite with a solution of rare earth elements under reduced pressure,
drying and calcining the P-rare earths-modified zeolite,
hydrothermally treating the P-rare earths-modified zeolite at 500-600° C. with water vapour, and
calcining the modified zeolite.

WO 03 020667 relates to a process of making olefin, particularly ethylene and propylene, from an oxygenate feed, comprising contacting an oxygenate feed with at least two different zeolite catalysts to form an olefin composition, wherein a first of the zeolite catalysts contains a ZSM-5 molecular sieve and a second of the zeolite catalysts contains a zeolite molecular sieve selected from the group consisting of ZSM-22, ZSM-23, ZSM-35, ZSM-48, and mixtures thereof. The ZSM-5 can be unmodified, phosphorus modified, steam modified having a micropore volume reduced to not less than 50% of that of the unsteamed ZSM-5, or various mixtures thereof. According to one embodiment, the zeolite is modified with a phosphorus containing compound to control reduction in pore volume. Alternatively, the zeolite is steamed, and the phosphorus compound is added prior to or after steaming. The amount of phosphorus, as measured on an elemental basis, is from 0.05 wt. % to 20 wt. %, and preferably is from 1 wt. % to 10 wt. %, based on the weight of the zeolite molecular sieve. Preferably, the atomic ratio of phosphorus to framework aluminum (i.e. in the zeolite framework) is not greater than 4:1 and more preferably from 2:1 to 4:1. Incorporation of a phosphorus modifier into the catalyst of the invention is accomplished, according to one embodiment, by contacting the zeolite molecular sieve either alone or the zeolite in combination with a binder with a solution of an appropriate phosphorus compound. The solid zeolite or zeolite catalyst is separated from the phosphorus solution, dried and calcined. In some cases, the added phosphorus is converted to its oxide form under such conditions. Contact with the phosphorus-containing compound is generally conducted at a temperature from 25° C. to 125° C. for a time from 15 minutes to 20 hours. The concentration of the phosphorus in the zeolite may be from 0.01 wt. % to 30 wt. %. This prior art discloses a non-formulated P-ZSM-5.

WO 2009 022990 A1 describes a catalyst composition for dehydration of an alcohol to prepare an alkene. The catalyst composition comprises a catalyst and a modifying agent which is phosphoric acid, sulfuric acid or tungsten trioxide, or a derivative thereof. There is no binder.

EP 2348004 A1 relates to the dehydration of ethanol to make ethylene and conversion of methanol to make a mixture of olefins (MTO). The catalyst is made by the following process: A ZSM-5 is steamed, P is introduced by contacting the steamed zeolite with an H3PO4 solution under reflux conditions, the P modified zeolite is extruded with a binder, calcium is introduced and the resulting catalyst is steamed two hours at 600° C. Alternatively the binder can be introduced before the introduction of P.

WO 2009-098262 A1 relates to the dehydration of ethanol to make ethylene. The catalyst is made by the following process: A ZSM-5 is steamed, P is introduced by contacting the steamed zeolite with an H3PO4 solution under reflux conditions, the P modified zeolite is extruded with a binder, there is no final steaming. There is no introduction of calcium.

EP 2082802 A1 relates to various petrochemical processes, the dehydration of alcohols to make an olefin having the same number of carbon atoms as the alcohol is not cited. Among the cited processes are the cracking of olefins and the conversion of oxygenates, e.g. methanol to make a mixture of ethylene, propylene, butenes and various hydrocarbons. The catalyst is made by the following process: A ZSM-5 is steamed, the steamed zeolite is extruded with a binder, P is introduced by contacting the steamed zeolite with an H3PO4 solution under reflux conditions, calcium is introduced and the resulting catalyst is steamed two hours at 600° C.

U.S. Pat. No. 4,356,338 relates to various petrochemical processes, the dehydration of alcohols to make an olefin having the same number of carbon atoms as the alcohol is not cited. The zeolite (ZSM-5) may be combined with a binder and is treated by a P containing component or steam or both steam and P containing component. There is no introduction of metals such as Ca in the catalyst. The said catalyst has a reduced coking.

It has now been discovered a new process to make P modified zeolites.

BRIEF DESCRIPTION OF THE INVENTION

The present invention relates, in a first embodiment, to a method to make a phosphorus modified zeolite comprising the following steps in this order,
a) providing a zeolite comprising at least one ten members ring in the structure, optionally making an ion-exchange,
b) optionally steaming said zeolite,
c) introducing phosphorus on the zeolite to introduce at least 0.1 wt % of phosphorus, said introduction being made by dry impregnation or chemical vapor deposition,
d) mixing said zeolite of step c) with at least a component selected among one or more binders and shaping additives,
e) shaping said mixture,
f) optionally introducing a metal, optionally simultaneously with step d),
g) optionally washing the catalyst,
h) optionally calcinating the catalyst,
i) steaming the catalyst, also referred to as the equilibration step.

The present invention relates, in a second embodiment, to a method to make a phosphorus modified zeolite comprising the following steps in this order,
a) providing a zeolite comprising at least one ten members ring in the structure, optionally making an ion-exchange,
b) optionally steaming said zeolite,
c) introducing phosphorus on the zeolite to introduce at least 0.1 wt % of phosphorus,
d) mixing said zeolite of step c) with at least a component selected among one or more binders and shaping additives,
e) shaping said mixture,
f) optionally introducing a metal, optionally simultaneously with step d),
g) optionally washing the catalyst,
h) optionally calcinating the catalyst,
i) steaming the catalyst, also referred to as the equilibration step, at a steaming severity (X) of at least about 2.

The above-described "steaming severity (X)" is an important, measurable and critical definition of treatment conditions for the steps d) which are useful in the instant invention.

"About" means that it could be slightly under 2. As explained hereunder the severity describes conditions of steaming to achieve a dealumination.

The matter is that the results of the steaming is a function of the nature of catalyst (type of zeolite, type of binder, Si/Al ratio, crystal size, crystallinity, structure defects, the presence of occluded contaminants etc) as well as of conditions of the treatment used. It is clear that the minimum severity is not an absolute value, considering the above parameters it can vary from a catalyst to another. The man skilled in the art can easily determine the minimum severity.

To be sure he can, by way of example, extend the duration of treatment and/or increase the temperature.

The critical parameters for the treatment include mainly steam partial pressure, temperature and duration of the treatment. If the objects of the treatment were similar nature the effect of the treatment is only a function of the "steaming severity".

A steaming or a hydrothermal treatment of the zeolite above 500° C. leads to a delumination of the framework. A degree of dealumination could be measured by $^{27}Al$, $^{29}Si$ MAS NMR, by acidity measurement (like TPD $NH_3$) or by any other means, which are well known in the prior art. A rate of the dealumination is defined mainly by mentioned above parameters, namely, steam partial pressure, temperature and duration of the treatment.

Thus, the "steaming severity (X)" is defined as a ratio of the dealumination rates between an experimental condition vs a standard condition.

Steaming performed at 600° C., in 100% of steam at atmospheric pressure during 2 h is selected as a standard condition for this invention.

The rate of dealumination (V) for the catalyst of invention is given by equation:

$$V \div Const \times P(H_2O)^{1.5} \times t_{st}/EXP(-0.03 \times T_{st}),$$

where $P(H_2O)$—steam partial pressure (P/Patm); $T_{st}$—steaming temperature in ° C.; $t_{st}$—time in hours (duration) of treatment and ÷ means proportional.

$$X(\text{The steaming severity}) = V_{experimental\ condition}/V_{standard\ condition}$$

This equation is valid in a steaming interval from 500° C. to 760° C.

So, the steaming severity value could be achieved even at lower temperature relative to the used in standard condition but for a higher time of duration.

The temperature 625° C. provides roughly 2 times higher steam severity vs the standard condition at equal time steam partial pressure and duration of the treatment.

If the temperature of the equilibration step is above 760° C. (out of the range), the duration of steaming is at least 0.1 h and the partial pressure of steam is at least 0.01 bar.

Advantageously in the second embodiment the temperature of the equilibration step is in the range 625 to 870° C.

In an embodiment the shaped zeolite (or molecular sieve) prior to step c) contains less than 1000 wppm of sodium.

In an embodiment the shaped zeolite (or molecular sieve) prior to step c) contains less than 1000 wppm of sodium, less than 1000 wppm of potassium and less than 1000 wppm of iron.

In an embodiment the shaped zeolite (or molecular sieve) prior to step c) contains less than 100 wppm of sodium.

In an embodiment the shaped zeolite (or molecular sieve) prior to step c) contains less than 100 wppm of sodium, less than 100 wppm of potassium and less than 500 wppm of iron.

The present invention also relates to the use of the catalyst made according to the above method in processes wherein said catalyst is operated in presence of steam at high temperature. "high temperature" means above 300° C. and up to 800° C. By way of example one can cite, the alcohol dehydration to convert at least an alcohol into the corresponding olefin, the olefin cracking to make lighter olefins, the MTO and the alkylation of aromatics by alcohols with olefins and/or alcohols, said process producing, by way of example, para-xylene, ethylbenzenes and cumene.

DETAILED DESCRIPTION OF THE INVENTION

As regards the zeolite of step a) containing at least one 10 members ring into the structure, one can cite the crystalline silicates. It is by way of example the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron.

Preferred zeolite structures are selected from the MFI, MTT, FER, MEL, TON, MWW, EUO, MFS.

In an embodiment, the zeolite is ZSM-5 with Si/Al atomic ratio ranging from 11 to 30, which has been made without direct addition of organic template.

In an embodiment, the zeolite is MFI zeolite with Si/Al atomic ratio ranging from 30 to 200.

The three-letter designations "MFI" and "MEL" each representing a particular crystalline silicate structure type as established by the Structure Commission of the International Zeolite Association. Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]:0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In an embodiment, the zeolite is pretreated by steam. The pretreatment is performed in the range 420 to 870° C., more preferably in the range 480 to 800° C. The water partial pressure may range from 13 to 100 kPa. The steam atmosphere preferably contains from 5 to 100 vol % steam with from 0 to 95 vol % of a gas, preferably nitrogen or air. The steam treatment is preferably carried out for a period of from 0.01 to 200 hours, more preferably from 0.05 to 50 hours, still more preferably for at least 0.1 hour and in a preferred way from 0.1 to 50 hours and in a more preferred way from 0.5 to 50 hours and still more preferred 1 to 50 hours.

The steam treatment tends to reduce the amount of tetrahedral aluminium in the crystalline silicate framework by forming alumina. Preferably, the amount of residual tetrahedral Al in the zeolite is between 60 to 95%. This value can be estimated by $^{27}$Al MAS NMR or TPD NH3. Optionally said alumina can be removed by leaching with an acid.

In an embodiment, the ZSM-5 with Si/Al atomic ratio ranging from 11 to 30, which has been made without direct addition of organic template, is pretreated by steam.

Additionally, if during the preparation of the zeolite alkaline or alkaline earth metals have been used, the molecular sieve might be subjected to an ion-exchange step. Conventionally, ion-exchange is done in aqueous solutions using ammonium salts or inorganic acids.

In an embodiment, the zeolite is subjected to dealumination such as about 10% by weight of the aluminium is removed. Such dealumination can be done by any conventional techniques known per se but is advantageously made by a steaming optionally followed by a leaching. The crystalline silicate having a ratio Si/Al of at least about 30 to 200 can be synthetized as such or it can be prepared by dealumination of a crystalline silicate with lower initial Si/Al ratio.

As regards the Ion-exchange of step a), purpose is to get advantageously a zeolite, before subjecting in a contact with a phosphatation agent, having less than 1000 wppm of alkali & alkali-earth metals, Na, K, Fe as well as less than 200 ppm of red-ox & noble elements such as Zn, Cr, Rh, Mn, Ni, V, Mo, Co, Cu, Cd, Pt, Pd, Ir, Ru, Re. This may be achieved by an optional back ion-exchange step known per se.

The ion exchange step is performed before the steaming of step b) if any.

In an embodiment, the molecular sieve has been treated to reduce alkali metal content to less than 100 ppm.

As regards the steaming of step b), it is also known as the pre-steaming by reference to the final steaming of step i). The treatment is performed in the range 420 to 870° C., more preferably in the range 480 to 800° C. The water partial pressure may range from 13 to 100 kPa. The steam atmosphere preferably contains from 5 to 100 vol % steam with from 0 to 95 vol % of a gas, preferably nitrogen or air. The steam treatment is preferably carried out for a period of from 0.01 to 200 hours, more preferably from 0.05 to 50 hours, still more preferably for at least 0.1 hour and in a preferred way from 0.1 to 50 hours and in a more preferred way from 0.5 to 50 hours and still more preferred 1 to 50 hours.

The steam treatment tends to reduce the amount of tetrahedral aluminium in the crystalline silicate framework by forming alumina. Preferably, the amount of residual tetrahedral Al in the zeolite is between 60 to 95%. This value can be estimated by $^{27}Al$ MAS NMR or TPD $NH_3$.

As regards the introduction of P of step c), said introduction of phosphorus can be performed under reduced or atmospheric pressure at temperature from 10 to 400° C. A non-limiting source of phosphorus can be provided in aqueous or non-aqueous medium.

In an embodiment, the non-aqueous medium is selected from the group containing ethanol, methanol or other alcohols.

The preferred techniques are impregnation and chemical vapour deposition. Said techniques are mandatory in the first embodiment of the invention.

These techniques imply a minimum waste to treat and allow maintaining substantially all phosphorus on the catalyst.

In an embodiment, the catalyst precursor (zeolite) is treated by a source of phosphorus injected into a steam flow. In this case, the phosphatation is performed under mild steaming condition with a steam flow containing phosphorus at 100-400° C.

In an embodiment, the phosphorus is introduced by a treatment of the catalyst precursor (zeolite) in a solution containing a source of phosphorus at temperature 25-100° C. for 0.1-96 h followed by filtering or evaporation.

In an embodiment amount of said acid solution containing P is advantageously between 2 and 10 liters per kg of zeolite plus binder. A typical period is around 0.5 to 24 hours. Advantageously the aqueous acid solution containing source of P has a pH of 3, advantageously 2, or lower.

Advantageously said aqueous acid solution is phosphorus acids, a mixture of phosphorus acids and organic or inorganic acid or mixtures of salts of phosphorus acids and organic or inorganic acids. The phosphorus acids or the corresponding salts can be of the phosphate ($[PO_4]^{3-}$, being tribasic), phosphite ($[HPO_3]^{2-}$, being dibasic), or hypophosphite ($[H_2PO_2]^{1-}$, being monobasic), type. Of the phosphate type also di or polyphosphates ($[P_nO_{3n+1}]^{(n+2)-}$) can be used. The contact of the zeolite+binder with the P containing component can be made under reflux conditions.

In a preferred embodiment the incipient wetness impregnation technique is used. In this case the phosphorus is introduced via impregnation using a limited amount of liquid water which is subjected to a contact with catalyst. This method is also known as the dry impregnation.

Incipient wetness (IW) or incipient wetness impregnation (IWI) is a commonly used technique for the synthesis of heterogeneous catalysts. Typically, the precursor (phosphorus-containing compounds) is dissolved in an aqueous or organic solution. The volume of solution, which is used for dissolution of the precursor, is substantially the same as the pore volume of catalyst precursor. Then the solution is added to a catalyst precursor. Capillary action draws the solution into the pores. The catalyst can then be dried and calcined to drive off the volatile components within the solution, depositing the phosphorus on the catalyst surface.

The sample before impregnation can be dried or calcined. The impregnation could be performed at room or elevated temperature (30-100° C.).

The adsorption capacity is typically measured by impregnating the dried extruded zeolite with water until the zeolite was completely wet. Weighing the zeolite before and after impregnation gives the absorption capacity:

$$\text{Absorption capacity}(\%) = \frac{\text{weight after impregantion} - \text{dry weight}}{\text{dry weight}} * 100$$

In an embodiment, H3PO4 solution is used for impregnation.

Advantageously, a mixture of H3PO4 with their ammonium salts providing a pH of the aqueous solution higher than 2.0 is used for impregnation In an embodiment, the sources of phosphorus are substantially metal free components, for example H3PO4, ammonium phosphates or organic P-compounds. "substantially metal free" means a metal proportion with has no adverse effect on the P introduction. By way of example this proportion can be below 1000 wppm.

The amount of phosphorus on the catalyst can be from 0.5 to 30 wt %, but preferably from 0.5 to 9 w %.

As regards step d), and the binder, it is selected so as to be resistant to the temperature and other conditions employed in the processes using the catalyst. The binder can be an inorganic material selected from silica, metal silicates, zirconia, borates, alumina, silica-aluminas, phosphates, for example amorphous aluminophosphates, calcium phosphates, clays, metal oxides such as $ZrO_2$ and/or metals, or gels including mixtures of silica and metal oxides.

In an embodiment, the binder is substantially neutral (inert) and it is selected from inorganic material selected from silica, non-acid alumina, amorphous aluminophosphates, metalphosphates, clays or a mixture of thereof. The neutral nature of the binder allow limiting secondary reactions leading to formation of heavy oxygenates and hydrocarbons, etane, acetaldehyde etc.

A particularly preferred binder for the catalyst of the present invention comprises silica. The relative proportions of the finely divided crystalline silicate material and the inorganic oxide of the binder can vary widely.

Non-limiting examples of silicon sources include silicates, precipitated silicas, for example, Zeosil range available from Rhodia, fumed silicas, for example, Aerosil-200 available from Degussa Inc., New York, N.Y., silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof.

Other suitable forms of amorphous silica include silica powders, such as Ultrasil VN3SP (commercially available from Degussa).

Other non-limiting examples of a suitable solid silica source are special granulated hydrophilic fumed silicas, mesoporous silica grade EXP & high surface area precipitated silica SIPERNAT from Evonik, HiSil 233 EP (available from PPG Industries) and Tokusil (available from Tokuyama Asia Pacific).

In addition, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol (available from Nyacol Nano Technologies, Inc. or PC) Corp.), Nalco (available from Nalco Chemical Company), Ultra-Sol (available from RESI Inc), Ludox (available from W.R. Grace Davison), NexSil (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required in order to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non limiting examples of silica sols that contain no detectable traces of sodium include Bindzil 2034DI, Levasil 200, Nalco 1034A, Ultra-Sol 7H or NexSil 20A.

In some case, silica dispersion prepared with alkylammonium might be useful. Non-limiting examples of commercially low sodium silica sols stabilized by ammonia or alkylammonium cations include LUDOX TMA (available from W.R. Grace Davison) or VP WR 8520 from Evonik. The silica sols with higher SiO2 content than 30% and even up to 50 wt %, for example W1250, W1836, WK341, WK7330 from Evonik are particularly preferred.

The preferred source of silicon is a silica sol or a combination of silica sol with precipitated or fumed silica.

Types of silica sols used to form a bound catalyst for use in alcohol dehydration process are commercially available as aquasols or organosols containing dispersed colloidal silica particles. For example, sodium silicate can be used as a silica sol. Otherwise, a silica gel, fumed or pyrogenic silica may also be used to provide a silica binder in the molecular sieve catalyst. Silicic acid is another possible source of silica. Advantageously, the binder contains low amount of sodium below 1000 ppm.

Clays are known to be essentially inert under a wide range of reaction conditions. Suitable clays include commercially available products such as kaolin, kaolinite, montmorillonite, attapulgite, saponite, and bentonite. These clays can be used as mined in their natural state, or they may also be employed in highly active forms, typically activated by an acid treatment procedure. Commercial suppliers of these clays include Thiele Kaolin Company, American Colloidal Co., and others.

Clays contribute to strength as a binder enhancing the attrition resistance properties of the catalyst particles, and clays in combination with binders contribute to the hardness of the particles. Clays also start as small particles and have a higher density, such that when combined with the molecular sieve and binder provide for denser particles, imparting the desirable characteristic of higher density.

Clays are used in this process to form a hardened product include, but are not limited to, kaolin, kaolinite, montmorillonite, saponite, bentonite, and halloysite.

In an embodiment, the binder material is often, to some extent, porous in nature and may be effective to promote the desired conversion of ethanol to ethylene. The binder might be a single amorphous entity, or a blend of two or more individual amorphous compounds.

In a related embodiment, the catalyst (zeolite+binder) has a volume of the pore between 30 Å and 1000 Å of at least 0.25 cc/g, advantageously between 0.25 and 1 cc/g preferably at least 0.26 cc/g, the most preferable between 0.27-0.92 cc/g. "cc" means cm3.

In an embodiment, the binder material possesses acid properties and may also promote conversion of the ethanol.

In referring to these types of binders that may be used, it should be noted that the term silica-alumina does not mean a physical mixture of silica and alumina but means an acidic and amorphous material that has been cogelled or coprecipitated. This term is well known in the art and is described, for example, in U.S. Pat. No. 3,909,450 BI; U.S. Pat. No. 3,274,124 B1 and U.S. Pat. No. 4,988,659 B I. In this respect, it is possible to form other cogelled or coprecipitated amorphous materials that will also be effective as either binder or filler materials. These include silica-zirconias, silica-thorias, silica-berylias, silica-titanias, silica-alumina-thofias, silica-alumina-zirconias, aluminophosphates, mixtures of these, and the like.

In another embodiment, catalyst contains alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

It is desirable to provide a catalyst having a good crush strength. This is because in commercial use, it is desirable to prevent the catalyst from breaking down into powder-like materials. Such oxide binders have been employed normally only for the purpose of improving the crush strength of the catalyst.

The catalyst composition may be prepared, as indicated above, by any of the methods described in the art. Advantageously, however, the catalyst particles are combined with the binder material initially by dry-mixing, then in a liquid, preferably water, preferably with a plasticizer, to yield a paste.

As plasticizer (shaping additive), there may be mentioned one that will be decomposed during any subsequent heat treatment, e.g., calcination. Suitable materials for this purpose include, for example, alkylated cellulose derivatives, hydroxyethylcellulose (HEC), tylose, ammonium alginate, polyvinyl pyrrolidone, glycerol, and polyethylene glycol.

In addition to enhancing the catalyst strength properties, the binder material allows the molecular sieve crystallite powder to be bound into larger particle sizes suitable for commercial catalytic processes. The formulation of the mixture b) may be formed into a wide variety of shapes including extrudates, spheres, pills, and the like.

The uniformly mixed paste may subsequently be shaped, for example by spray drying to yield microspheres, pelletizing or, preferably, by extrusion.

The paste is then extruded, for example in a piston extruder, into strings, for example cylindrical, dried, again calcined, and chopped into pieces of a desired length.

As regards the proportions of the P modified zeolite, the one or more binders and shaping additives, advantageously the proportion of the zeolite is from 5 to 95 w % of the catalyst. The catalyst comprises the zeolite and at least a component selected among one or more binders and shaping additives. The amount of zeolite which is contained in the catalyst ranges more advantageously from 15 to 90 weight percent of the total catalyst, preferably 20 to 85 weight percent of the catalyst.

Once the molecular sieve catalyst composition is shaped, and in a substantially dry or dried state, a heat treatment, for example calcination, is advantageously performed to harden and/or activate the composition. Therefore the heat treatment is preferably carried out at a temperature of at least 400° C., for a period of from 1 to 48 hours. Calcination may be carried out, for example, in a rotary calciner, fluid bed calciner, or a batch oven.

As regards step f), the introduction of metal, it can be one or more metals. Advantageously said metals are selected among alkaline earth or rare earth metals. The alkaline earth or rare earth metal M is preferably selected from one or more of: Mg, Ca, Sr, Ba, La, Ce. More preferably, M is an alkaline earth metal. Most preferably, M is Ca. Particularly in the case of P-modification via steaming and leaching, M can be a rare earth metal such as La and Ce. Advantageously the metal is introduced in a soluble form.

The M-containing component is preferably in the form of an organic compound, a salt, hydroxide or oxide. The compound is preferably in a solubilized form when bringing it into contact with the molecular sieve. Alternatively, the solution of the M-containing compound can be formed after bringing the molecular sieve in contact with said compound.

Possible M-containing compounds include compounds such as sulphate, formate, nitrate, acetate, halides, oxyhalides, borates, carbonate, hydroxide, oxide and mixtures thereof. One can cite calcium carbonate.

Those M-containing compounds, which are poorly water-soluble, can be dissolved to form a well-solubilized solution by heating and/or by modifying the pH of the solution by addition of phosphoric, acetic or nitric acid or corresponding ammonium salts of said acids.

As regards step g), a washing step can be envisaged. In accordance with the present invention, the catalyst is treated with water for a period of time from 0.1 to 48 hours, preferably for a period of time from about 0.5 to 36 hours and most preferably from about 1 to 24 hours. The water was at a temperature between about 20° C. and 180° C., preferably between about 20° C. and 100° C. and most preferably between about 25° C. and 60° C. By way of example the water can be at 30° C. Following the water treatment, the catalyst may be dried at about >60° C. Optionally, the water can contain at least one dissolved solid selected from the group consisting of ammonium chloride, ammonium phosphate, ammonium sulfate, ammonium acetate, ammonium carbonate, ammonium nitrate and mixtures thereof.

As regards step h), said calcination can be made in air or an inert gas, typically at a temperature of from 350 to 900° C. for a period of from 1 to 48 hours. Optionally the air or an inert gas may contain steam in concentration from 10 to 90 vol %.

As regards step i), in the first embodiment of the invention it can be performed in the range 420 to 870° C., preferably in the range 480 to 870° C., preferably from 625 to 870° C. and more preferably from 700 to 800° C., still more preferably in the range 720 to 800° C. Alternatively it can be performed in the range 420 to 600° C., preferably 420 to 580° C.

In the second embodiment of the invention it is performed by steaming at steaming severity above about 2 or alternatively at temperature above 625° C., preferably from 625 to 870° C. and more preferably from 700 to 800° C. still more preferably in the range 720 to 800° C. The water partial pressure may range from 13 to 100 kPa. The steam atmosphere preferably contains from 5 to 100 vol % steam with from 0 to 95 vol % of a gas, preferably nitrogen or air. The steam treatment is preferably carried out for a period of from 0.01 to 200 hours, preferably from 0.05 to 50 hours, more preferably for at least 0.1 hour and in a preferred way from 0.1 to 50 hours, and in a more preferred way from 0.5 to 50 hours and still more preferred 1 to 50 hours.

As regards the dehydration process to convert an alcohol into an olefin, this process has been described in a lot of patent applications. One can cite WO/2009/098262, WO/2009/098267, WO/2009/098268 and WO 2009/098269, the content of which is incorporated in the present application. The alcohol is any alcohol provided it can be dehydrated to the corresponding olefin. Advantageously the alcohol has two or more carbon atoms. The corresponding olefin is an olefin having the same number of carbons as the alcohol. By way of example mention may be made of alcohols having from 2 to 10 carbon atoms. Advantageously the invention is of interest for ethanol, propanol, butanol and phenylethanol.

As regards the cracking of olefins, more precisely the present invention relates to a process for cracking an olefin-rich hydrocarbon feedstock which is selective towards light olefins in the effluent. In particular, olefinic feedstocks from refineries or petrochemical plants can be converted selectively so as to redistribute the olefin content of the feedstock in the resultant effluent. Said cracking of an olefin-rich feedstock is often referred in the following description and claims as OCP (Olefin Cracking Process). As regards the hydrocarbon feedstock containing one or more olefins sent to the OCP reactor, in accordance with the present invention, cracking of olefins is performed in the sense that olefins in a hydrocarbon stream are cracked into lighter olefins and selectively into propylene. The feedstock and effluent preferably have substantially the same olefin content by weight. Typically, the olefin content of the effluent is within ±15 wt %, more preferably ±10 wt %, of the olefin content of the feedstock. The feedstock may comprise any kind of olefin-containing hydrocarbon stream. The feedstock may typically comprise from 10 to 100 wt % olefins and furthermore may be fed undiluted or diluted by a diluent, the diluent optionally including a non-olefinic hydrocarbon. In particular, the olefin-containing feedstock may be a hydrocarbon mixture containing normal and branched olefins in the carbon range $C_4$ to $O_{10}$, more preferably in the carbon range $C_4$ to $O_6$, optionally in a mixture with normal and branched paraffins and/or aromatics in the carbon range $C_4$ to $C_{10}$. Typically, the olefin-containing stream has a boiling point of from around −15 to around 180° C. With regards to the OCP process, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention.

As regards the MTO, said process produces light olefins such as ethylene and propylene as well as heavy hydrocarbons such as butenes. Said MTO process is the conversion of methanol or dimethylether by contact with a molecular sieve which can be a P modified zeolite.

As regards the alkylation of aromatic compounds with olefins and alcohols, said process produces, by way of example, para-xylene, ethylbenzenes and cumene. Alkylation of aromatic, for example, toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process.

One skilled in the art will also appreciate that the olefins made by the dehydration process of the present invention can be, by way of example, polymerized. When the olefin is ethylene it can be, by way of example, polymerized to form polyethylenes,
dimerized to butene and then isomerised to isobutene, said isobutene reacting with ethanol to produce ETBE,
dimerized to butane followed by reacting with ethylene via methatesis to produce propylene;
converted to propylene over metal, acid or bifunctional catalyst, used for alkylation of benzene to form ethylbenzene,
dimerised to 1-butene, trimerised to 1-hexene or tetramerised to 1-octene, said alpha-olefins comonomers are further reacted with ethylene to produce polyethylene
dimerised to 1-butene, said 1-butene is isomerised to 2-butene and said 2-butene is further converted with ethylene by metathesis reaction into propylene and said propylene can be polymerised to polypropylene,
converted to ethylene oxide and glycol or
converted to vinyl chloride.

The present invention relates also to said polyethylenes, polypropylene, propylene, butene, hexane, octene, isobutene, ETBE, vinyl chloride, ethylene oxide and glycol.

When the olefin is propylene it can be, by way of example, polymerized to form polypropylene,
used for alkylation of aromatics etc. . . . .

EXAMPLES

Example 1

A sample of zeolite ZSM-5 (Si/Al=12) in NH4-form (contained 250 ppm of Na & synthesized without template) was blended with a silica binder in a ratio 80:20 followed by addition of extrusion additives and shaping. A final Na content in the catalyst was 320 ppm.
The extruded sample was dried for 2 h at 140° C., calcined for 2 h at 600° C. followed by steaming at 550° C. for 6 h in 100% steam.
Steamed solid was incipient wetness impregnated with an aqueous solution of phosphoric acid to introduce about 3 wt % of phosphorus to the catalyst. The impregnated solid was dried for 16 h at 110° C.
Then, the phosphated sample was incipient wetness impregnated with a solution of calcium nitrate obtained by dissolution of calcium carbonate to introduce about 1 wt % of calcium to the solid. The impregnated solid was dried for 16 h at 110° C.
Resulted catalyst containing 2.8 wt % of phosphorus and 0.8% of calcium was steamed at 600° C. for 2 h in 100% of steam (steaming severity 1). The sample is hereinafter identified as sample A.
Resulted catalyst containing about 2.8 wt % of phosphorus and 0.8% of calcium was steamed at 750° C. for 1 h in 100% of steam (steaming severity 45). The sample is hereinafter identified as sample B. Total pore volume measured by mercury intrusion porosimetry is 0.36 cm3/g.
Catalyst tests were performed on 1 ml of catalyst grains (35-45 meshes) loaded in a tubular reactor with internal diameter 11 mm. A mixture 25 wt % EthOH/75 wt % $H_2O$ was subjected to a contact with catalyst described in the example I in a fixed bed reactor at 380° C., WHSV=7 $h^{-1}$ P=2 bara. The results are given in table 1 hereunder. The values are the weight percents on carbon basis.

Example 2

A sample of zeolite ZSM-5 (Si/Al=12) in NH4-form (containing 250 ppm of Na & synthesized without template) was blended with a silica binder in a ratio 80:20 followed by addition of extrusion additives and shaping. A final Na content in the catalyst was 320 ppm.
The extruded sample was dried for 16 h at 110° C., calcined for 10 h at 600° C. followed by steaming at 550° C. for 6 h in 100% steam.
Steamed shaped zeolite was then contacted with an aqueous solution of $H_3PO_4$ (85% wt) Under conditions of incipient wetness. Then 1 g of $CaCO_3$ was introduced. After stirring during 30 min, the system is cooled down at room temperature and the excess of solution is removed by filtration without washing. The recovered solid is dried at 110° C. for 16 h followed by steaming at 600° C. for 2 h in 100% of steam (steaming severity 1).
Resulted catalyst contained about 1.7 wt % of phosphorus and 0.4 wt % of calcium. The sample is hereinafter identified as sample C
The performances of the catalyst were then evaluated under the same operating conditions as described above, using 1 ml of catalyst (35-45 mesh) loaded in a tubular reactor with internal diameter 11 mm. A mixture of 25 wt % EtOH/75 wt % $H_2O$ has been processed on catalyst C, in a fixed bed reactor at 380° C., WHSV=7 $h^{-1}$ P=2 bara. The results are given in table 1. The values are the weight percents on carbon basis.

Example 3

A sample of zeolite ZSM-5 (Si/Al=12) in NH4-form (containing 250 ppm of Na & synthesized without template) was blended with a silica binder in a ratio 80:20 followed by addition of extrusion additives and shaping. A final Na content in the catalyst was 320 ppm.
The extruded sample was dried for 16 h at 110° C., calcined for 10 h at 600° C. followed by steaming at 550° C. for 6 h in 100% steam.
12 g of steamed solid was incipient wetness impregnated with an aqueous solution containing 1.54 g of NH4H2PO4. The impregnated solid was dried for 16 h at 110° C.
Then, the phosphated sample was incipient wetness impregnated with a solution of calcium nitrate obtained by dissolution of 0.3 g calcium carbonate in nitric acid. The impregnated solid was dried for 16 h at 110° C., followed by steaming at 600° C. for 2 h in 100% of steam (steaming severity 1).
Resulted catalyst contained about 2.54 wt % of phosphorus and 0.82 wt % of calcium. The sample is hereinafter identified as sample D.
The performances of the catalyst were then evaluated under the same operating conditions as described above, using 1 ml of catalyst (35-45 mesh) loaded in a tubular reactor with internal diameter 11 mm. A mixture of 25 wt % EtOH/75 wt % $H_2O$ has been processed on catalyst D, in a fixed bed reactor at 380° C., WHSV=7 $h^{-1}$ P=2 bara. The results are given in table 1. The values are the weight percents on carbon basis.

TABLE 1

| Sample | A | B | C | D |
|---|---|---|---|---|
| P (bara) | 2 | 2 | 2 | 2 |
| T (° C.) | 380 | 380 | 380 | 380 |
| WHSV (H-1) | 7 | 7 | 7 | 7 |
| EtOH conversion (% wt CH2) | 99.9 | 99.8 | 99.9 | 99.9 |
| DEE | 0.0 | 0.0 | 0.0 | 0.0 |
| Acetaldyde | 0.31 | 0.17 | 0.17 | 0.13 |
| EtOH | 0.10 | 0.20 | 0.05 | 0.05 |
| Yield on C-basis (% wt CH2) | | | | |
| CH4 | 0.00 | 0.00 | 0.00 | 0.00 |
| C2 | 0.13 | 0.06 | 0.11 | 0.12 |
| C2= | 97.9 | 99.0 | 97.3 | 97.4 |
| C3= | 0.56 | 0.07 | 0.7 | 0.8 |
| C4+ olef | 0.86 | 0.48 | 1.6 | 1.4 |
| Unknown | 0.10 | 0.06 | 0.07 | 0.08 |
| Selectivity on C-basis (% wt CH2) | | | | |
| C2= | 98.0 | 99.20 | 97.4 | 97.4 |
| C2's cut purity (%) | 99.87 | 99.94 | 99.88 | 99.87 |

Example 4

A sample of zeolite ZSM-5 (Si/Al=12) in NH4-form (contained 250 ppm of Na & synthesized without template) was blended with a binder containing silica and kaolin in a ratio 70:10:20 followed by addition of extrusion additives and shaping.
The extruded sample was dried for 2 h at 140° C., calcined for 10 h at 600° C. followed by steaming at 550° C. for 6 h in 100% steam.
Steamed solid was incipient wetness impregnated with an aqueous solution of phosphoric acid to introduce about 3 wt % of phosphorus to the catalyst. The is impregnated solid was dried for 16 h at 110° C.
Then, the phosphated sample was incipient wetness impregnated with a solution of calcium nitrate obtained by dissolution of calcium carbonate to introduce about 1 wt % of calcium to the solid. The impregnated solid was dried for 16 h at 110° C.
Resulted catalyst containing 2.94 wt % of phosphorus and 0.8% of calcium was steamed at 750° C. for 2 h in 100% of steam (steaming severity 90). The sample is hereinafter identified as sample E.

Example 5

A sample of zeolite ZSM-5 (Si/Al=12) in NH4-form (synthesized without template) was calcined for 10 h at 600° C. followed by steaming at 550° C. for 6 h in 100% steam.
100 g of steamed solid was incipient wetness impregnated (dry impregnated) with an aqueous solution containing 9.86 g of phosphoric acid. The impregnated solid was dried for 16 h at 110° C.
Then, 16 g of the phosphated sample was extruded with 4 g of silica binder and 0.4 g of $CaCO_3$.
The resulted catalyst was calcined at 600° C. for 10 h followed by steaming at 600° C. for 2 h in 100% of steam (steaming severity 1). The sample is hereinafter identified as sample F.

Example 6 (OCP Test)

Catalyst tests were performed on 0.8 g of catalyst grains (35-45 meshes) loaded in the tubular reactor. The feedstock which contains substantially non cyclic olefins C4 (~60%) was subjected to catalytic cracking in the presence of catalyst in a fixed bed reactor at $T_{in}$-550° C., WHSV=16 $h^{-1}$, P=1.5 bara. The results are in table 2. The values in the table 2 are the average catalyst performance for 1-10 hours-on-stream given in weight percents on carbon basis.
The data given below illustrate good cracking activity and high selectivity of the P-zeolite in C4 olefins conversion to propylene and ethylene.

TABLE 2

| Sample | E | F |
|---|---|---|
| P (bara) | 1.5 | 1.5 |
| $T_{in}$ (° C.) | 550 | 550 |
| WHSV ($h^{-1}$) | 16 | 16 |
| C4 olefins conversion, % | 65.4 | 65.2 |
| Purity C3's, % | 94.9 | 96.0 |
| Yield on C-basis, % | | |
| Methane | 0.07 | 0.14 |
| Aromatics | 1.2 | 1.4 |
| Propane | 1.0 | 0.8 |
| Ethylene | 3.5 | 3.4 |
| Propylene | 19.5 | 19.1 |

The invention claimed is:

1. A method to make a phosphorus modified zeolite comprising, in this order:
   a) providing a zeolite comprising at least one ten member ring in the structure thereof, and optionally making an ion-exchange;
   b) steaming said zeolite;
   c) introducing phosphorus on the zeolite to introduce at least 0.1 wt % of the phosphorus, wherein said introduction is performed by incipient wetness impregnation (IWI) whereby the zeolite is contacted with a volume of a solution comprising a phosphorus-containing compound, wherein the volume of the solution is substantially the same as a pore volume of the zeolite;
   d) mixing said zeolite of step c) with at least a component selected among one or more binders and shaping additives;
   e) shaping said mixture to form a catalyst;
   f) introducing an alkaline earth or rare earth metal M to the catalyst in a soluble form, optionally simultaneously with step d);
   g) optionally washing the catalyst;
   h) optionally calcinating the catalyst;
   i) steaming the catalyst made from steps (d) through (h) at a temperature ranging from 420-to 870° C., wherein the catalyst has a volume of pores between 30 Å and 1000 Å of at least 0.25 cc/g.

2. The method of claim 1, wherein the zeolite of step b) contains less than 100 wppm of sodium.

3. The method of claim 1, wherein the zeolite of step b) contains less than 100 wppm of sodium, less than 100 wppm of potassium and less than 500 wppm of iron.

4. The method of claim 1, wherein the zeolite of step b) contains less than 1000 wppm of sodium.

5. The method of claim 1, wherein the zeolite of step b) contains less than 1000 wppm of sodium, less than 1000 wppm of potassium and less than 1000 wppm of iron.

6. The method of claim 1, wherein the zeolite s MFI, MTT, FER, MEL, TON, MWW, EUO, or MFS.

7. The method of claim 1, wherein the zeolite Is ZSM-5 with Si/Al atomic ratio ranging from 11 to 30, and wherein the zeolite has been made without direct addition of organic template.

8. The method of claim 1, wherein the zeolite is MFI with Si/Al atomic ratio ranging from 30 to 200.

9. The method of claim 1, wherein the amount of phosphorus on the catalyst is from 0.5 to 30 wt %.

10. The method of claim 1, wherein the amount of phosphorus on the catalyst is from 0.5 to 9 w %.

11. The method of claim 1, wherein the alkaline earth or rare earth metal M is Mg, Ca, Sr, Ba, La, Ce, or combinations thereof.

12. A method to make a phosphorus modified zeolite comprising, in this order:
    a) providing a zeolite comprising at least one ten member ring in the structure thereof, and optionally making an ion-exchange;
    b) optionally steaming said zeolite;
    c) introducing phosphorus on the zeolite to introduce at least 0.1 wt % of the phosphorus using incipient wetness impregnation whereby the zeolite is contacted with a volume of a solution comprising a phosphorus-containing compound, wherein the volume of the solution is substantially the same as a pore volume of the zeolite;
    d) mixing said zeolite of step c) with at least a component selected among one or more binders and shaping additives;
    e) shaping said mixture to form a catalyst;
    f) introducing an alkaline earth or rare earth metal M to the catalyst in a soluble form, optionally simultaneously with step d);
    g) optionally washing the catalyst;
    h) optionally calcinating the catalyst; and
    i) steaming the catalyst at a steaming severity (X) of at least about 2, wherein the catalyst has a volume of pores between 30 Å and 1000 Å of at least 0.25 cc/g.

13. The method of claim 12, wherein the steaming of step i) is performed at a temperature ranging from 700 to 800° C.

14. The method of claim 12, wherein the steaming of step i) is performed at a temperature ranging from 720 to 800° C.

15. The method of claim 12, wherein the zeolite of step b) contains less than 100 wppm of sodium.

16. The method of claim 12, wherein the zeolite of step b) contains less than 100 wppm of sodium, less than 100 wppm of potassium and less than 500 wppm of iron.

17. The method of claim 12, wherein the zeolite of step b) contains less than 1000 wppm of sodium.

18. The method of claim 12, wherein the zeolite of step b) contains less than 1000 wppm of sodium, less than 1000 wppm of potassium and less than 1000 wppm of iron.

19. The method of claim 12, wherein the zeolite is MFI, MTT, FER, MEL, TON, MWW, EUO, or MFS.

20. The method of claim 12, wherein the zeolite is ZSM-5 with Si/A atomic ratio ranging from 11 to 30, and wherein the zeolite has been made without direct addition of organic template.

21. The method of claim 12, wherein the zeolite is MFI with Si/Al atomic ratio ranging from 30 to 200.

22. The method of claim 12, wherein the amount of phosphorus on the catalyst is from 0.5 to 30 wt %.

23. The method of claim 12, wherein the amount of phosphorus on the catalyst is from 0.5 to 9 w %.

24. The method of claim 12, wherein the alkaline earth or rare earth metal M is Mg, Ca, Sr, Ba, La, Ce, or combinations thereof.

\* \* \* \* \*